United States Patent
Morefield et al.

(10) Patent No.: US 6,231,838 B1
(45) Date of Patent: May 15, 2001

(54) TASTE MASKING WITH SILICON DIOXIDE

(75) Inventors: Elaine Marie Morefield; Sauwaluxana Tongaree, both of Richmond, VA (US)

(73) Assignee: American Home Products Corporation, Madison, NJ (US)

( * ) Notice: Subject to any disclaimer, the term of this patent is extended or adjusted under 35 U.S.C. 154(b) by 0 days.

(21) Appl. No.: 09/464,048

(22) Filed: Dec. 15, 1999

(51) Int. Cl.$^7$ .............................. A61K 47/00; A61K 7/44
(52) U.S. Cl. ........................ 424/60; 514/974; 514/770
(58) Field of Search ................... 514/568, 770, 514/546, 974; 424/470, 59

(56) References Cited

U.S. PATENT DOCUMENTS

| | | | |
|---|---|---|---|
| 4,910,023 | * 3/1990 | Botzolakis et al. | 424/470 |
| 5,243,021 | * 9/1993 | Langer et al. | 528/272 |
| 5,510,250 | * 4/1996 | Aga et al. | 435/97 |
| 5,571,503 | * 11/1996 | Mausner | 424/59 |
| 5,618,522 | * 4/1997 | Kaleta et al. | 424/60 |
| 5,672,339 | * 9/1997 | Soyama et al. | 424/63 |
| 5,677,442 | * 10/1997 | Maruta et al. | 536/123.13 |
| 5,750,090 | * 5/1998 | Yoshida et al. | 424/59 |
| 5,785,984 | * 7/1998 | Kurihara et al. | 424/439 |
| 5,827,508 | * 10/1998 | Tanner et al. | 424/59 |
| 5,843,407 | * 12/1998 | El-Nokaly et al. | 424/64 |
| 6,027,746 | * 2/2000 | Lech | 424/455 |
| 6,036,945 | * 3/2000 | Deblasi et al. | 424/59 |

FOREIGN PATENT DOCUMENTS

| | | | |
|---|---|---|---|
| 0 345 787 A2 | 12/1989 | (EP) | A61K/9/18 |
| 0 345 787 B1 | 11/1992 | (EP) | A61K/9/18 |
| 635218 | * 1/1995 | (EP) . | |
| 9415580 | * 7/1994 | (WO) . | |
| WO 94/28870 | 12/1994 | (WO) | A61K/9/00 |

* cited by examiner

Primary Examiner—William R. A. Jarvis
Assistant Examiner—Vickie Kim
(74) Attorney, Agent, or Firm—Steven H. Flynn

(57) ABSTRACT

The present invention provides a composition which includes one or more organic suncreens and colloidal silicon dioxide. Preferably, the colloidal silicon dioxide is prewetted with a liquid, such as liquid silicone. In another embodiment, the present invention provides a composition for topical application to the lips or oval cavity. The composition includes a topically applicable anhydrous base; a malflavored organic sunscreen; and a malflavored organic sunscreen taste-masking effective amount of colloidal silicon dioxide. In yet another embodiment, a method of preparing the composition of the present invention is provided. The method includes the steps of (a) mixing silicon dioxide and a liquid, such as silicone; (b) adding the mixture of step (a) to a melted anhydrous base material; (c) adding an organic sunscreen to the mixture of step (b); and (d) cooling the mixture of step (c).

11 Claims, No Drawings

TASTE MASKING WITH SILICON DIOXIDE

FIELD OF THE INVENTION

The present invention relates to the removal or masking of the taste of malflavored organic sunscreens in lip and oral cavity application products.

BACKGROUND OF THE INVENTION

Lip application products usually contain flavoring and sweetening agents to mask any malflavor of ingredients in the product. These agents, however, frequently fail to effectively mask the malflavor.

European Patent Application No. 345,787 discloses a method for fabricating tablets by a wet granulation process. The process involves absorbing colloidal silicon dioxide onto an unpleasant flavored drug. Once the granulation process is completed, the mixture is dried in an oven, milled, and tableted. The resulting tablets each contain from 5 to 20 percent by weight of silicon dioxide based on 100 percent weight of the tablet.

World Patent Application No. WO 94/28870 discloses an improved chewable cold/sinus medication which is incorporated onto an absorbant material. The absorbant material contains from about 5 to about 95 percent by weight of silicon dioxide based on 100 percent weight of total drug adsorbate preparation.

There is a continuing need to provide taste-masking agents for malflavored lip and oral cavity application products.

SUMMARY OF THE INVENTION

The present invention provides a composition which includes one or more organic suncreens and colloidal silicon dioxide. Preferably, the colloidal silicon dioxide is prewetted with a liquid, such as liquid silicone.

In another embodiment, the present invention provides a composition for topical application to the lips or oral cavity. The composition includes a topically applicable anhydrous base; one or more malflavored organic sunscreens; and a malflavored organic sunscreen taste-masking effective amount of colloidal silicon dioxide.

In yet another embodiment, a method of preparing these compositions is provided. The method includes the steps of (a) mixing silicon dioxide and a liquid, such as liquid silicone; (b) adding the mixture of step (a) to a melted anhydrous base material; (c) adding an organic sunscreen to the mixture of step (b); and (d) cooling the mixture of step (c).

DETAILED DESCRIPTION OF THE INVENTION

The present invention is directed to a composition which removes or masks the taste of malflavored organic suncreens with colloidal silicon dioxide. Malflavored organic sunscreens include, but are not limited to, unpleasant, off flavored, and bitter tasting organic sunscreens. Generally, these compositions are applied topically to the lips or oral cavity.

According to one embodiment of the present invention, the composition includes (a) a topically applicable anhydrous base; (b) a malflavored organic sunscreen; and (c) a malflavored organic sunscreen taste-masking effective amount of colloidal silicon dioxide. Preferably, the colloidal silicon dioxide is wetted colloidal silicon dioxide.

The anhydrous base may include, but is not limited to, petrolatum; silicones; oils, such as aloe vera oil; lanolin; vitamin E; waxes, such as carnauba wax, wax paraffin, white wax, and waxenol; cetyl alcohol; oleyl alcohol; preservatives; flavorants; colorants; and any combination of any of the foregoing. The composition broadly contains from about 65 to about 95 percent by weight and preferably from about 75 to about 90 percent by weight of anhydrous base, based upon 100 percent by weight of total composition.

Organic sunscreens suitable for use in the present invention include, but are not limited to, octocrylene, octylmethoxycinnamate, octylsalicylate, oxybenzone, and any combination of any of the foregoing. The composition generally contains from about 1 to about 40 percent by weight and preferably from about 3.5 to about 25 percent by weight, based upon 100 percent by weight of total composition.

Suitable colloidal silicon dioxides include, but are not limited to, fumed silica, such as Aerosil™ 200 available from Degussa of Ridgefield Park, N.J. and Cab-O-Sil™ available from Cabot Corp. of Kokoma, Ind. The colloidal silicon dioxide preferably has a density of from about 0.04 to about 0.12 g/cc and a surface area of from about 130 to about 390 $m^2/g$. According to one preferred embodiment, the colloidal silicon dioxide has a density of about 0.05 g/cc and a surface area of about 200 $m^2/g$.

Colloidal silicone dioxide is generally a fine fluffy material which is often difficult to mix with other ingredients without producing environmentally hazardous dust. The present inventors have discovered that when colloidal silicon dioxide is prewetted with a liquid, such as liquid silicone, it may be mixed with other ingredients without producing hazardous dust. Other suitable liquids include, but are not limited to, polyphenylmethylsiloxane; cyclomethicone; dimethicone; dimethicone copolyol; mineral oil; liquid sunscreens, such as octocrylene and octylmethoxycinnamate; glycerin; propylene glycol; polyethylene glycol; and any combination of any of the foregoing. The silicon dioxide is therefore wetted with a liquid before being mixed with other components of the composition.

The composition contains a malflavored organic sunscreen taste-masking effective amount of colloidal silicon dioxide. The composition typically contains from about 0.05 to about 2 percent by weight and preferably from about 0.1 to about 2 percent by weight of colloidal silicon dioxide, based upon 100 percent weight of total composition. At concentrations above 1 percent, the silicon dioxide may impart a metallic taste to the composition.

Other flavorants, including, but not limited to, sweetening agents, such as saccharin, may be included in the composition. The composition may also contain other adjuvants including, but not limited to, colorants; non-organic sunscreens, such as titanium dioxide; perfume; and any combination of any of the foregoing.

The composition may be formed or incorporated into various lip and oral cavity application products, such as lip balm, lip ointment, cold sore ointment, lipstick, lip gloss, sunscreen face stick, lip gel, and lip lotion. The composition of the present invention may be topically applied to the lips or the oral cavity of an animal, such as a human, in need of the composition to prevent or treat sun exposure of the lips or oral cavity.

The composition of the present invention typically may be prepared as follows. Silicon dioxide is mixed, i.e., prewetted, with a liquid, such as liquid silicone. The prewetted silicon dioxide is added to a melted anhydrous base material. Typically, the anhydrous base material is melted at a temperature ranging from about 150 to about 160° F. The mixture is preferably maintained at a temperature of from about 150 to about 160° F. One or more organic sunscreens are added to the wetted silicon dioxide/anhydrous base material mixture. The mixture is then cooled to produce a composition of the present invention.

DESCRIPTION OF THE PREFERRED EMBODIMENTS

The following example is intended to describe the present invention without limitation.

EXAMPLE 1

The formulation in Table 1 below was prepared as follows.

TABLE 1

| Ingredient | percent w/w |
| --- | --- |
| Aerosil ™ 200[1] | 0.10 |
| Aloe vera oil | 1.00 |
| Carnauba wax | 1.00 |
| Cetyl alcohol | 0.50 |
| Flavor | 2.85 |
| Isopropyl lanolate | 1.50 |
| Isopropyl myristate, NF | 1.00 |
| Lanolin, modified, USP[2] | 1.00 |
| Methylparaben, NF | 0.10 |
| Octocrylene | 7.00 |
| 2-Octyldodecanol | 4.50 |
| Octylmethoxycinnamate | 7.50 |
| Octyl salicylate | 5.00 |
| Oleyl alcohol | 1.75 |
| Oxybenzone, USP | 5.00 |
| Polyphenylmethylsiloxane 556[3] | 2.25 |
| Propylparaben, NF | 0.06 |
| Saccharin | 0.05 |
| Titanium dioxide, EUT | 1.25 |
| Vitamin E acetate, USP | 1.50 |
| Waxenol ™ 801[4] | 3.00 |
| Wax paraffin | 20.0 |
| White petrolatum, USP | 30.0 |
| White wax, NF | 2.00 |
| Total | 100 |

[1]Aerosil ™ 200 is a silicone available from Degussa of Ridgefield Park, N.J.
[2]Lanolin, modified, USP is superfine lanolin available from Croda of New York, NY.
[3]Polyphenylmethylsiloxane 556 is phenyl trimethicone available from Dow Corning of Midland, MI.
[4]Waxenol ™ 801 is arachidyl propionate available from Akzo Inc. of Sayreville, NJ.

Wax paraffin, white wax NF, modified lanolin USP, cetyl alcohol, and carnauba wax were melted in a stainless steel jacketed kettle heated to about 160–180° F. Once the ingredients were sufficiently melted, they were mixed.

Isopropyl myristate was heated to about 150–160° F. with stirring in a beaker. Methylparaben and propylparaben were added to the beaker while the temperature was maintained at about 150–160° F. The mixture was mixed with a magnetic stir bar until the parabens were uniformly dispersed in the solution.

Polyphenylmethylsiloxane 556 was added to a tank containing Aerosil™ 200 and mixed with a lightnin mixer available from Lightnin Mixers of Rochester, N.Y., for about 15–30 minutes, until the Aerosil™ 200 was completely dispersed.

White petrolatum USP, Waxenol™ 801, octyldodecanol NF, isopropyl lanolate, polyphenylmethylsiloxane 556, oleyl alcohol, aloe vera oil, saccharin, the isopropyl myristate/methylparaben/propylparaben mixture, and the polyphenylmethylsiloxane 556/Aerosil™ 200 mixture were added to the kettle. The mixture in the kettle was heated to about 160–180° F. in order to melt the components in the mixture. Once the mixture was sufficiently melted, it was mixed until all the components had melted. Octylmethoxycinnamate, octocrylene, octyl salicylate, oxybenzone, titanium dioxide, and vitamin E acetate were added to the kettle with stirring. The temperature of the mixture was maintained at about 160–180° F., but did not exceed 180° F. Mixing was continued for at least 15 minutes, until all of the components were completely melted and the mixture was homogeneous. The mixture was then cooled to about 140–150° F.

A flavorant was added to the mixture and mixed for at least 5 minutes, while the temperature was maintained at about 140–150° F. Mixing was continued until the flavorant was uniformly distributed throughout the mixture.

The mixture had very little bitter aftertaste when applied to the lips.

All patents, publications, applications, and test methods mentioned above are hereby incorporated by reference. Many variations of the present matter will suggest themselves to those skilled in the art in light of the above detailed description. All such obvious variations are within the patented scope of the appended claims.

What is claimed is:

1. An anhydrous composition for topical application to the lips or oral cavity, said composition comprising:
    (a) a topically applicable anhydrous base;
    (b) from about 10 to about 40% by weight of malflavored organic sunscreen; and
    (c) a malflavored organic sunscreen taste masking effective amount of pre-wetted colloidal silicon dioxide, based upon 100% total weight of composition.

2. A composition as defined in claim 1, wherein said pre-wetted colloidal silicon dioxide is wetted with a liquid silicone.

3. A composition as defined in claim 1, wherein the colloidal silicon dioxide is wetted with polyphenylmethylsiloxane, cyclomethicone, dimethicone, dimethicone copolyol, mineral oil, liquid sunscreens, glycerin, propylene glycol, polyethylene glycol, or any combination of any of the foregoing.

4. A composition as defined in claim 1, wherein said pre-wetted colloidal silicon dioxide is wetted with polyphenylmethylsiloxane.

5. A composition as defined in claim 1, wherein said sunscreen is selected from the group consisting of octocrylene, octylmethoxycinnamate, octylsalicylate, oxybenzone, and any combination of any of the foregoing.

6. A composition as defined in claim 1, wherein the amount of colloidal silicon dioxide ranges from about 0.05 to about 2 percent by weight based upon 100 percent total weight of composition.

7. A composition as defined in claim 1, wherein the amount of colloidal silicon dioxide ranges from about 0.1 to about 2 percent by weight based upon 100 percent total weight of composition.

8. A composition as defined in claim 1, wherein said colloidal silicon dioxide is selected from the group consisting of silicone, fumed silica, or a combination thereof.

9. A composition as defined in claim 1, further comprising:
    (d) a flavorant,
    (e) a colorant, (f) a non-organic sunscreen, (g) perfume, or (h) any combination of any of the foregoing.

10. A method for preventing or treating symptoms or damage due to sun exposure of the lips of an animal in need of said prevention or treatment, said method comprising topically applying to a surface of said lips, a composition as defined in claim 1.

11. A method of masking the malflavor of a topical composition comprising malflavored organic sunscreen, the method comprising adding a taste-masking effective amount of colloidal silicon dioxide to the composition, wherein the topical composition after the addition step comprises from about 10 to about 40% by weight of the malflavored organic sunscreen based upon 100% total weight of composition.

* * * * *